United States Patent [19]

Balzer

[11] Patent Number: 5,605,651
[45] Date of Patent: Feb. 25, 1997

[54] EMULSIFIERS FOR THE PREPARATION OF OIL-IN-WATER EMULSIONS OF ESSENTIAL OILS USABLE IN COSMETICS OR MEDICINE

[75] Inventor: Dieter Balzer, Haltern, Germany

[73] Assignee: Huels Aktiengesellschaft, Marl, Germany

[21] Appl. No.: 390,424

[22] Filed: Feb. 17, 1995

Related U.S. Application Data

[63] Continuation of Ser. No. 860,076, Mar. 30, 1992, abandoned.

[30] Foreign Application Priority Data

Mar. 30, 1991 [DE] Germany ............... 41 10 506.0

[51] Int. Cl.$^6$ .................. B01J 13/00; C11D 1/66
[52] U.S. Cl. ............ 252/312; 424/401; 424/76.4; 514/938; 510/136
[58] Field of Search .................. 252/312, 351, 252/356, 174.17, 550, 108, 173; 424/455, 76.1, 76.4, 283.1, 195.1, 196.1, 197.1, 401

[56] References Cited

U.S. PATENT DOCUMENTS

| | | | |
|---|---|---|---|
| 3,721,633 | 3/1973 | Ranauto | 252/527 |
| 4,396,520 | 8/1983 | Payne et al. | 252/89.1 |
| 4,483,787 | 11/1984 | Jones et al. | 252/551 |
| 4,488,981 | 12/1984 | Urfer et al. | 252/174.17 |
| 4,536,318 | 8/1985 | Cook et al. | 252/174.17 |
| 4,668,422 | 5/1987 | Malik et al. | 252/174.17 |
| 4,784,844 | 11/1988 | Thimineur et al. | 424/65 |
| 4,800,080 | 1/1989 | Grollier et al. | 424/195.1 |
| 4,834,903 | 5/1989 | Roth et al. | 252/174.17 |
| 4,923,685 | 5/1990 | Wuelknutz et al. | 424/54 |
| 4,985,154 | 1/1991 | Balzer et al. | 252/8.554 |
| 5,063,057 | 11/1991 | Spellman et al. | 424/401 |
| 5,100,573 | 3/1992 | Balzer | 252/174.17 |
| 5,133,897 | 7/1992 | Balzer | 252/312 |
| 5,139,771 | 8/1992 | Gerstein | 424/195.1 |
| 5,154,855 | 10/1992 | Sekiguchi et al. | 252/312 |
| 5,308,531 | 5/1984 | Urfer et al. | 252/174.17 |

FOREIGN PATENT DOCUMENTS

| | | |
|---|---|---|
| 0306652 | 3/1989 | European Pat. Off. . |
| 0306651 | 3/1989 | European Pat. Off. . |
| 0306650 | 3/1989 | European Pat. Off. . |
| 0384983 | 9/1990 | European Pat. Off. . |
| 0418479 | 3/1991 | European Pat. Off. . |
| 0444262 | 9/1991 | European Pat. Off. . |
| 0444267 | 9/1991 | European Pat. Off. . |
| 0448799 | 10/1991 | European Pat. Off. . |
| 0486786 | 5/1992 | European Pat. Off. . |
| 2546768 | 12/1984 | France . |
| 2663847 | 1/1992 | France . |
| WO90/05772 | 3/1990 | WIPO . |
| WO91/13961 | 9/1991 | WIPO . |
| WO92/06778 | 4/1992 | WIPO . |
| WO92/07543 | 5/1992 | WIPO . |

OTHER PUBLICATIONS

Derwent Abstract, AN–81–44617D/25, (corresponding to DE 3 045 083 and US 4,7844,844), 1981.
Hackh's Chemical Dictionary, Third Edition, (The Blakiston Company, Philidelphia, 1950) pp. 314–315 and 627.
F. A. Hughes and B. W. Lew, "Physical and Functional Properties of Some Higher Alkyl Polyglucosides", *JAOCS*, 47(5)(1970) pp. 162–167.
Derwent Abstract AN—90—164596/22 (corresponding to WO 90/05772).

*Primary Examiner*—Richard D. Lovering
*Assistant Examiner*—Daniel S. Metzmaier
*Attorney, Agent, or Firm*—Oblon, Spivak, McClelland, Maier & Neustadt, P.C.

[57] ABSTRACT

Emulsifier systems containing alkyl polyglycosides of the formula $$R-O-Z_n$$

wherein R is an alkyl group and Z is a glycoside group are useful in the preparation of oil-in-water emulsions for cosmetic or medical preparations. The emulsifier systems optionally contain co-emulsifiers, oils and/or water.

13 Claims, No Drawings

EMULSIFIERS FOR THE PREPARATION OF OIL-IN-WATER EMULSIONS OF ESSENTIAL OILS USABLE IN COSMETICS OR MEDICINE

This application is a Continuation of application Ser. No. 07/860,076, filed on Mar. 30, 1992, now abandoned.

BACKGROUND OF THE INVENTION

1. Field of the Invention

The invention relates to emulsifiers for the preparation of emulsions of essential oils or mixtures thereof with other oils or fatty bases used in cosmetics or medicine.

2. Discussion of the Background

Formulations of this type find manifold use in bath oils, bath emulsions (bath milk) and cosmetic cleansing fluids which contain essential oils. Since some of the essential oils also have antiseptic actions, the invention also targets medical bath or embrocation fluids. The oil phase of these fluids can be either emulsified or solubilized, which is frequently achieved by higher emulsifier concentrations.

Emulsions of this type have been marketed for a long time. The emulsifiers used are surfactants, for example alcohol sulphates, betaines, oxethylates of fatty alcohols, phosphoric acid esters, sorbitan esters, etc. or mixtures thereof. Because of the particular cosmetic or medical use of these oil-in-water emulsions, an exceptionally high skin and mucosa tolerance is a prerequisite for the emulsifiers used.

SUMMARY OF THE INVENTION

Accordingly, one object of the invention is to provide emulsifiers which have an exceptionally high skin and mucosa tolerance coupled with high emulsifiability for the corresponding oil or fatty bases customarily used in cosmetics or medicine.

This and other objects which will become apparent from the following specification have been achieved by the present emulsifier which contains alkyl polyglycosides of the formula $R-O-Z_n$ where R is a saturated or unsaturated alkyl group and Z is an oligoglycoside group.

DETAILED DESCRIPTION OF THE PREFERRED EMBODIMENTS

The invention relates to emulsifier systems for the preparation of oil-in-water emulsions of essential oils or as a mixture with a oil base, which are usable in cosmetics or medicine and which are characterized by containing 80–100 wt % alkyl polyglycosides of the formula (I)

$$R-O-Z_n \qquad (I)$$

in which R represents a straight-chain or branched, saturated or unsaturated alkyl group having 8–16 carbon atoms, Z represents a glycoside group and n is on average 1–5 and 20–0 wt % of co-emulsifiers.

It has been found, surprisingly, that these exceptionally mild surfactants, used alone or in some cases in combination with small amounts of surfactants customary in cosmetics or medicine, are outstanding emulsifiers for essential oils and with other oil bases customary in cosmetics or medicine.

This is the more surprising since it is known from DE-OS 39 25 846 that alkyl polyglycosides are outstandingly suitable as emulsifiers for polysiloxane or polysiloxane/paraffin oil emulsions, that is to say for oils which are characterized by hydrophilic/lipophilic balance (HLB) values very much lower than those which apply in the case of essential oils.

It has also been observed that high shear forces are not required in order to prepare these oil-in-water emulsions, which are stable on storage. In some cases, especially in the presence of high concentrations, transparent systems (presumably microemulsions) are formed by this procedure.

Alkyl polyglycosides are generally known to be gentle to the skin. As disclosed by G. Proserpio and G. Vianello, "Applicazioni tensio-cosmetiche di un nuovo glucoside, Revista Italiana, essenze, profumi, piante officinali, aromi, saponi, cosmetici, aerosol", No. 10 October 1974, pages 567 to 572, the alkyl polyglycoside Triton CG 110 ($C_8$–$C_{10}$-alcohol-based), for example, is better tolerated by the skin than many other surfactants customary in cosmetic formulations. F. A. Hughes and B. W. Lew, J.A.O.C.S., 47:162 (1970) also describe the outstanding skin and mucosa tolerance of alkyl polyglycosides.

Alkyl polyglycosides which may be used according to the present invention are those of formula (I)

$$R-O-Z_n \qquad (I)$$

in which R represents a straight-chain or branched, saturated or unsaturated alkyl group having 8–16 carbon atoms, Z represents a glycoside group and n has an average value of 1–5.

Straight-chain, saturated alkyl polyglycosides having 10 to 14 carbon atoms and a degree of glycosidation between 1.1 and 2 are particularly preferred.

The alkyl polyglycosides used according to the invention can be prepared by known processes wholly or partly on the basis of raw materials which undergo further reaction. For example, dextrose is reacted in the presence of an acid catalyst with n-butanol to form butyl oligoglycoside mixtures, which are subjected to transglycosidation with long-chain alcohols, likewise in the presence of an acid catalyst, to give the desired alkyl oligoglycoside mixtures. The formula of the product can be varied within certain limits. The alkyl group R is determined by the choice of the long-chain alcohol.

On economic grounds, the surfactant alcohols having 8 to 16 carbon atoms, which are accessible industrially, for example naturally occurring fatty alcohols from the hydrogenation of fatty acids or fatty acid derivatives, Ziegler alcohols and optionally also oxo alcohols, are preferred.

The oligoglycosyl group $Z_n$ is determined on the one hand by the choice of the carbohydrate and on the other hand by the adjustment of the average degree of oligomerization (n), for example in accordance with DE-OS 19 43 689. Polysaccharides, oligosaccharides and monosaccharides, for example starch, maltodextrins, dextrose, galactose, mannose, xylose, etc., can be reacted under known conditions to give alkyl polyglycosides. The industrially available carbohydrates, starch, maltodextrins and dextrose are particularly preferred. Since the alkyl polyglycoside syntheses which are economically worthwhile do not proceed regioselectively or stereoselectively, the alkyl polyglycosides are always mixtures of oligomers, which, in turn, are mixtures of various isomeric forms. They are present together with α-glycoside and β-glycoside bonds in pyranose and furanose forms. The carbon atoms involved in glycoside bonds between two saccharide groups may also vary. Due to the method of synthesis, the alkyl polyglycosides may also contain impurities such as residual alcohols, monosaccharides, oligosaccharides and oligoalkyl polyglycosides.

Alkyl polyglycosides used according to the invention may also be prepared by admixing alkyl polyglycosides with alkyl monoglycosides. The latter can be isolated or concentrated in alkyl polyglycosides, for example in accordance with EP-A 0 092 355 using polar solvents, such as acetone.

The degree of glycosidation is appropriately determined by means of $^1$H-NMR.

Ecologically, the alkyl polyglycosides are some of the most environmentally biodegradable surfactants. Values of 95 to 97% were obtained in tests to determine the biodegradability (Coupled Unit Test, DOC Measurement). The toxicity data, with LD 50 (rat)>10,000 mg/kg, LC 50 (golden orfe) 12–40 mg/l and EC 50 (Daphnia) 30–110 mg/l for, in each case, two $C_{10}C_{12}$-alkyl polyglycoside and $C_{12}C_{14}$-alkyl polyglycosides also indicate outstanding environmental characteristics compared with many other surfactants.

The situation is similar with regard to the data for skin and mucosa irritation, which for $C_{10}C_{12}$-, $C_{12}C_{14}$- and $C_{12}C_{13}$-alkyl polyglycosides having degrees of glycosidation of between 1.2 and 1.7, are extremely favorable compared with all other surfactants tested. The surfactants used in the present invention, alone or with other surfactants (co-emulsifiers) are therefore useful in cosmetic and medical applications and environmentally preferred. Combining the emulsifier of the present invention with other surfactants or co-emulsifiers reduces the irritation potential of the co-emulsifier.

The alkyl polyglycoside content in such an emulsifier system (mixture of emulsifiers) is 80 to 99.9 wt %, preferably 85 to 99 wt. % and the co-emulsifier content is 20–0.1 wt. % preferably 15–1 wt. %.

Co-emulsifiers according to the invention are as far as possible mild surfactants, which in combination with the main emulsifiers, the alkyl polyglycosides, lead to finely dispersed emulsions which are stable on storage. They are used when the alkyl polyglycoside or combinations of various alkyl polyglycosides do not on their own lead to the desired results. Their amounts are usually small, compared with the main emulsifier, so that their somewhat greater incompatibility with regard to skin and the environment is substantially reduced by the alkyl polyglycoside which is present in excess.

Co-emulsifiers according to the invention are fatty alcohol sulphates, fatty alcohol ether-sulphates, alkyl sulphonates, carboxymethylated fatty alcohol oxethylates, fatty alcohol (ether) phosphates, fatty alcohol ethersulphosuccinates, alkyl betaines, fatty alcohol oxethylates, fatty acid oxethylates, fatty acid esters of polyhydric alcohols or of ethoxylated polyhydric alcohols (sorbitan esters), sugar fatty acid esters, fatty acid partial glycerides, glycerides with fatty acids and polybasic carboxylic acids, etc. The chain length of the saturated or unsaturated alkyl chain is in each case $C_8$–$C_{20}$, preferably $C_{10}$–$C_{18}$, and the cations of the anionic surfactants are Na, K, $NH_4$, $C_2$–$C_3$-alkanolammonium or Mg. The degrees of ethoxylation are between 1 and 5 (preferably between 2 and 4) mol of ethylene oxide/mol in the case of the fatty alcohol ether-sulphates, between 2 and 15 (preferably 3–10) mol of ethylene oxide/mol in the case of the carboxylated oxethylates, between 1 and 6 (preferably 2–4) mol of ethylene oxide/mol in the case of the fatty alcoholether-sulphosuccinates, between 0 and 12 (preferably 2–10) mol of ethylene oxide/mol in the case of the fatty alcohol ether phosphates, between 3 and 1 and 10 (preferably 4–25) mol of ethylene oxide/mol in the case of the fatty alcohol oxethylates, between 2 and 25 (preferably 3–20) mol of ethylene oxide/mol in the case of the fatty acid oxethylates and between 3 and 30 (preferably 4–20) mol of ethylene oxide/mol in the case of the fatty acid esters of polyhydric ethoxylated alcohols.

In addition to these surfactants and their mixtures, further products are also suitable, such as, for example, those mentioned by B. Idson in "Surfactants in Cosmetics", Ed. M. M. Rieger, Surfactant Science Series, Vol. 16, pp. 1 to 28.

The co-emulsifier content in the emulsifier system is between 0.1 and 20 wt. %, preferably between 1.0 and 15 wt. %.

Further constituents of the emulsion are the oil or base to be emulsified, water, and optionally electrolytes, colorants, preservatives, so-called fat restorers, such as, for example, ethoxylated partial glycerides, etc.

The oil or base to be emulsified consists of essential oils, such as, for example, lavender oil, pine-needle oil, spruce-needle oil, eucalyptus oil, orange oil, oil of rosemary, oil of thyme, lemon oil, etc., or mixtures thereof, frequently as an admixture with a cosmetic oil base such as groundnut oil, olive oil, paraffin oil, isopropyl myristate, etc.

A preferred procedure for the preparation of the emulsion comprises dissolving or dispersing the emulsifier according to the invention at room temperature in the essential oil or mixture of essential oil and oil base and then dispersing this solution or dispersion in the aqueous phase under low shear. In the case of another preferred method, the emulsifier is dissolved or dispersed in an aqueous phase and this phase is then mixed into the oil base under low shear. The emulsions obtained in both processes are usually of low to moderate viscosity (1–500 mPa.s), of bluish-white to white appearance, in so far as the oil base is colorless, and completely stable on storage even at elevated temperature (up to about 50° C.). In some cases, especially in the presence of increased emulsifier concentrations, transparent bases, presumably microemulsions, are formed which when added to bath water form a clear solution or a milky emulsion. Depending on the emulsifier system chosen, there can be extensive foaming, which is desired in many cases.

The emulsifier concentration (alkyl glycoside alone or as a mixture with co-emulsifiers), based on the essential oil and cosmetic oil base, is usually between 1 and 99.9 wt. %, preferably 1 and 80 wt. %, most preferably between 2 and 60%.

The water/oil ratio is usually between 100 and 0.2, preferably between 50 and 0.3.

Other features of the invention will become apparent in the course of the following descriptions of exemplary embodiments which are given for illustration of the invention but are not intended to be limiting thereof.

EXAMPLES

Example 1

2.5 g of $C_{12}C_{14}$-alkyl polyglyoside (APG), degree of glycosidation 1.3, were dissolved in 10 g of orange oil (orange terpene: Dragoco) at room temperature, with gentle stirring. The solution was then introduced into 87.5 g of water, with gentle stirring. A finely dispersed emulsion formed immediately and was unchanged even after standing for 3 weeks.

Example 2

12.5 g of $C_{12}C_{14}$-APG, degree of glycosidation 1.3, were dissolved in 50 g of orange oil and the solution was combined with 37.5 g of water as in Example 1. An opalescent, very finely dispersed emulsion formed which did not change over the course of 1 week even at elevated temperature (50° C.).

Example 3

2.5 g of $C_{10}C_{12}$-APG, degree of glycosidation 1.2, were finely dispersed in 10 g of aniseed oil (Dragoco), with gentle stirring. The slightly turbid solution was then introduced into 87.5 g of water. A finely dispersed, bluish-white emulsion formed immediately, which was stable even after prolonged standing.

Example 4

45 g of $C_{10}C_{12}$-APG, degree of glycosidation 1.7, were dissolved in 40 g of alcoholic extract of rosemary (Kneipp), 1 g of SOFTIGEN® 767 (fat restorer) was added and the solution was combined with 14 g of water. A clear fluid having a viscosity of 36 mPa.s and a clear point of 4° C. was formed.

Example 5

2.4 g of $C_{12}C_{14}$-APG, degree of glycosidation 1.3, and 0.1 g of $C_{12}C_{14}$-fatty alcohol sulphate were dispersed in 10 g of eucalyptus oil (Dragoco) with gentle stirring. The turbid solution was then combined with 87.5 g of water. An opalescent, very finely dispersed emulsion formed, which was unchanged even after prolonged standing (3 weeks) at 40° C.

Example 6 (Comparison Example)

2.5 g of $C_{12}C_{14}$-APG, degree of glycosidation 1.3, were dispersed in 10 g of eucalyptus oil. When the turbid solution was then introduced into water, phase separation took place immediately. The same result was obtained when, in place of alkyl polyglycoside, $C_{12}C_{14}$-fatty alcohol sulphate was used as the only emulsifier.

Example 7

2.4 g of $C_{12}C_{14}$-APG, degree of glycosidation 1.3, and 0.1 g of $C_{12}C_{18}$-fatty alcohol sulphate were dissolved in 10 g of spruce needle oil (Dragoco). The slightly turbid solution was then combined with 87.5 g of water, with gentle stirring. An opalescent, extremely finely dispersed emulsion was formed which showed no change whatsoever even after storage for 1 month at 50° C.

However, if the two surfactants were each used individually as the sole emulsifier, immediate phase separation took place.

Example 8

1.25 g of $C_{10}C_{12}$-APG having a degree of glycosidation of 1.2 and 1.25 g of IMWITOR® 370 (citric acid ester of mono- and diglycerides of edible fatty acids) were dissolved in 87.5 g of water, with stirring. On introduction of 10 g of spruce-needle oil a very finely dispersed, opalescent emulsion which was stable on storage was formed.

When IMWITOR® 370 was used as the sole emulsifier, separation took place immediately.

Example 9

2.35 g of $C_{12}C_{14}$-APG having a degree of glycosidation of 1.3 and 0.15 g of $C_{12}C_{14}$-alcohol sulphate were dispersed in a mixture of 4 g or orange oil and 6 g of isopropyl myrisrate, with gentle stirring. On introducing the slightly turbid solution into 87.5 g of water, a bluish-white finely dispersed emulsion formed.

Example 10

2.35 g of $C_{12}C_{14}$-APG having a degree of glycosidation of 1.3 and 0.15 g of $C_{12}C_{14}$-alcohol sulphate were dissolved in a mixture of 5 g of eucalyptus oil and 5 g of isopropyl myristate, with stirring. On introducing the slightly turbid solution into 87.5 g of water, a white emulsion formed which was stable on storage.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method for producing an oil-in-water emulsion usable in cosmetics or topical medical preparations, which is storage-stable at elevated temperature, said emulsion comprising an essential oil, which method comprises:

introducing an emulsifier-and-oil system into water, or introducing an emulsifier-and-water into oil, wherein the oil comprises an essential oil in an amount of from 10% to about 50% by weight based on the total weight of the emulsion optionally in admixture with a cosmetic oil base, with the use of shear forces, wherein the emulsifier consists essentially of:

(a) 80 to 99.9 wt. % of an alkyl polyglycoside of the formula (I):

$$R\text{—}O\text{—}Z_n \qquad (I)$$

wherein R is a straight-chain or branched, saturated or unsaturated alkyl group having 8–16 carbon atoms, Z is a glycoside group and n has an average value of 1–5, and (b) from 0.1 to 20 wt. % of a co-emulsifier selected from the group consisting of an anionic, cationic and betainic co-emulsifier.

2. The method of claim 1 wherein the method comprises introducing the emulsifier-and-oil system into water.

3. The method of claim 2, wherein the emulsifier comprises 85 to 99 wt. % of the polyglycoside and 1.0 to 15 wt. % of the co-emulsifier.

4. The method of claim 2, wherein the oil comprises an essential oil and a cosmetic oil base.

5. The method of claim 4, wherein the concentration of the emulsifier and co-emulsifier is 1–99.9 wt. % based on the essential oil and cosmetic oil base.

6. The method of claim 1 wherein the method comprises introducing the emulsifier-and-water system into the oil.

7. The method of claim 6, wherein the emulsifier comprises 85–99 wt. % of the polyglycoside and 1.0 to 15 wt. % of the co-emulsifier.

8. The method of claim 6, wherein the oil comprises an essential oil and a cosmetic oil base.

9. The method of claim 8, wherein the concentration of the emulsifier and co-emulsifier is 1–99.9 wt. % based on the essential oil and cosmetic oil base.

10. An oil-in-water emulsion usable in cosmetics or topical medical preparations, comprising:

water, an essential oil usable in cosmetics or topical medical preparations optionally in admixture with a cosmetic oil base, said essential oil being present in an amount of from about 10% to about 50% by wt. based upon the total weight of the emulsion; and an emulsifier consisting essentially of:

(a) 80 to 99.9 wt. % of an alkyl polyglycoside of the formula (I):

$$R\text{—}O\text{—}Z_n \qquad (I)$$

wherein R is a straight-chain or branched, saturated or unsaturated alkyl group having 8–16 carbon atoms, Z is a glycoside group and n has an average value of 1–5, and (b) from 0.1 to 20 wt. % of a co-emulsifier selected from the group consisting of an anionic, cationic, and betainic co-emulsifier.

11. The emulsion of claim 10, wherein R is a straight-chain, saturated alkyl group having 10 to 14 carbon atoms and n has a value of 1.1 to 2.0.

12. The emulsion of claim 10, wherein the emulsifier comprises 85 to 99 wt. % of the polyglycoside and 1.0 to 15 wt. % of the co-emulsifier.

13. The emulsion of claim 10, wherein the essential oil is selected from the group consisting of lavender oil, pine-needle oil, aniseed oil, spruce-needle oil, eucalyptus oil, orange oil, oil of rosemary, oil of thyme, lemon oil and mixtures thereof.

* * * * *